United States Patent
Yamazaki et al.

[11] Patent Number: 5,990,113
[45] Date of Patent: *Nov. 23, 1999

[54] MONOHYDRATES OF AMINOBENZENESULFONIC ACID DERIVATIVES AND METHOD FOR PREPARING THEREOF

[75] Inventors: Chika Yamazaki; Tadao Sato, both of Ibaraki; Tatsuo Nagano, Kanagawa, all of Japan

[73] Assignee: Mitsubishi Chemical Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/767,062

[22] Filed: Dec. 16, 1996

[30] Foreign Application Priority Data

Dec. 15, 1995 [JP] Japan .................................. 7-326648
Dec. 15, 1995 [JP] Japan .................................. 7-327068

[51] Int. Cl.$^6$ ..................... A61K 31/495; A61K 31/55; C07D 295/096; C07D 243/08
[52] U.S. Cl. .................... 514/255; 514/218; 540/575; 544/392; 544/394; 544/395
[58] Field of Search .................... 544/392, 394, 544/395; 514/255

[56] References Cited

U.S. PATENT DOCUMENTS 4,411,904 10/1983 Pattison .................................. 544/392
5,053,409 10/1991 Okushima et al. .................... 514/255
5,457,107 10/1995 Kaufman .............................. 514/236.2
5,486,517 1/1996 Downing et al. ....................... 514/253

FOREIGN PATENT DOCUMENTS 0 390 654 10/1990 European Pat. Off. .
2 503 611 8/1975 Germany .
2 126 598 3/1984 United Kingdom .

OTHER PUBLICATIONS

Kitamura et al, Chemical Abstracts, vol. 111, No. 23519, 1989.
Okujima et al., Chemical Abstracts, vol. 117, No. 21, Nov. 23, 1992, Abstract No. 212524h, p. 850 JP 04 139 127.

Primary Examiner—Emily Bernhardt
Attorney, Agent, or Firm—Wenderoth, Lind & Ponack, L.L.P

[57] ABSTRACT

A monohydrate of an aminobenzenesulfonic acid derivative represented by the following formula (I), for example, 2-(1-piperazinyl)-5-methylbenzenesulfonic acid, is substantially free from weight change due to moisture absorption and can be weighed accurately in manufacturing a pharmaceutical composition for the treatment of heart diseases comprising said monohydrate.

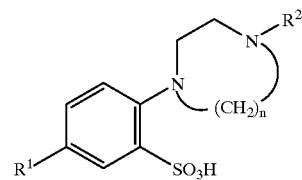

5 Claims, 5 Drawing Sheets

MONOHYDRATES OF AMINOBENZENESULFONIC ACID DERIVATIVES AND METHOD FOR PREPARING THEREOF

FIELD OF THE INVENTION

The present invention relates to the monohydrates of aminobenzenesulfonic acid derivatives, pharmaceutical compositions comprising said hydrates as active ingredients, and methods for preparing the monohydrates of the aminobenzenesulfonic acid derivatives.

BACKGROUND ART

The aminobenzenesulfonic acid derivatives represented by the following formula (I):

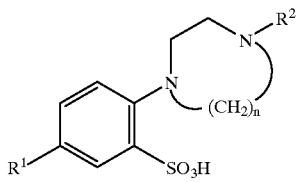

wherein $R^1$ represents a hydrogen atom, a $C_1$–$C_6$ alkyl group, a $C_3$–$C_7$ cycloalkyl group, a halogenated $C_1$–$C_4$ alkyl group, a halogen atom, or a $C_6$–$C_{12}$ aryl group; $R^2$ represents a hydrogen atom, a $C_1$–$C_6$ alkyl group, or a $C_7$–$C_{12}$ aralkyl group which may have one or more substituents selected from the group consisting of cyano group, nitro group, a $C_1$–$C_6$ alkoxy group, a halogen atom, a $C_1$–$C_6$ alkyl group, and amino group; and n represents an integer of from 1 to 4, are known to have inhibitory activities on intracellular hyperaccumulation of $Ca^{2+}$ (the Japanese Patent Unexamined Publication (KOKAI) No. (Hei)3-7263/1991). It has been also revealed that these compound are useful for the preventive and therapeutic treatment of ischemic heart diseases such as myocardial infarction or angina pectoris, cardiac failure, hypertension, arrhythmia and the like [the Japanese Patent Unexamined Publication (KOKAI) Nos. (Hei)3-7263/1991 and (Hei)4-139127/1992].

Among these compounds, 2-(1-piperazinyl)-5-methylbenzenesulfonic acid (the substance disclosed in Example 1 of the Japanese Patent Unexamined Publication (KOKAI) No. (Hei)3-7263/1991 and disclosed as Compound No. 12 in Preparation Example 1 of the Japanese Patent Unexamined Publication (KOKAI) No. (Hei)4-139127/1992) remarkably inhibits the inflow of calcium ions into cardiac muscle cells and is highly safe, and thus the compound is expected to be extremely useful as an active ingredient of a medicament for preventive and therapeutic treatment of heart diseases.

The methods for preparation of these compounds are disclosed in the Japanese Patent Publication (KOKOKU) No. (Hei)6-86438/1994, and according to these methods, the compounds of the above formula (I) are obtained as anhydrous crystals. However, according to the research by the inventors of the present invention, it was found that these anhydrous crystals are hygroscopic and may finally form monohydrates, when being left alone, by gradually absorbing moisture to gain weight. When the inventors conducted research particularly focusing on the preparation of formulations to provide 2-(1-piperazinyl)-5-methylbenzenesulfonic acid as a medicament for therapeutic and preventive treatment of heart disease, they faced problems that the substance could not be accurately weighed because it gradually absorbed moisture and varied in weight during manufacturing processes, and that constant formulations could not be stably manufactured because the contents of the active ingredient fluctuated from lot to lot of resulting formulations. In order to provide medicaments comprising the aforementioned aminobenzenesulfonic acid derivatives as active ingredients, it is thus desired that monohydrates instead of anhydrous crystals are used from the viewpoints of manufacturing and distributing medicaments being stable and having guaranteed constant qualities.

The Japanese Patent Unexamined Publication (KOKAI) Nos. (Hei) 3-7263/1991 and (Hei)4-139127/1992 disclose the presence of acid addition salts and base addition salts of the aforementioned aminobenzenesulfonic acid derivatives. However, the publications neither teach nor suggest that these compounds have properties to form hydrates. Furthermore, although the publications specifically disclose 2-(1-piperazinyl)-5-methylbenzenesulfonic acid in the free form (anhydrous crystal), they neither teach nor suggest as to whether or not the compound forms a monohydrate.

Generally, for the preparation of hydrates from anhydrous crystals, such methods are used, for example, (1) a method in which an anhydrous crystal is left in a steam-humidified room so as to be appropriately moistened; or (2) a method in which an anhydrous crystal is actively sprayed with humidified steam so as to be appropriately moistened. However, when large amounts of hydrates are manufactured, the above method (1) requires a prolonged period of time for humidification and it also causes difficulties that constant hydrates can hardly be manufactured, because sweat, formed in the steam room or the container, leads to partially uneven humidification. The method (2) also causes problems that constant hydrates can hardly be manufactured because of partially uneven humidification when an anhydrous crystal is insufficiently dispersed. In addition, in both of the methods (1) and (2), it is difficult to control the conditions for humidification, and accordingly, it is very likely that moisture is absorbed more than the desired amount that equates to the anhydrous crystal. In that case, a problem arises that the anhydrous crystal must be prepared all over again. The inventors of the present invention tried to prepare a monohydrate basically according to the method (1), and as described in the Reference Example which follows, they confirmed that the method had problems, for example, that the production of monohydrate required a long period of time and sweat was formed in the steam room or the container and the sweat had to be frequently wiped.

SUMMARY OR THE INVENTION

The inventors of the present invention examined the causes for the above problems, and as a result, they found that the anhydrous crystal of 2-(1-piperazinyl)-5-methylbenzenesulfonic acid gradually converted to monohydrate by uptaking one molecule of water as water of crystallization while contacting moisture in air and water used in the drug manufacturing process. The inventors also found that the monohydrate once formed was stable and free from weight variation by hygroscopicity, and that the monohydrate can be accurately weighed when used in a formulation process and thus a pharmaceutical composition containing a constant content of the active ingredient can be provided. The present invention was achieved on the basis of these findings. In addition, the inventors of the present invention conducted various studies on convenient methods for preparing monohydrates of the aminobenzenesulfonic acid derivatives, and as a result, succeeded in achieving the present invention.

The present invention thus provides a monohydrate of an aminobenzenesulfonic acid derivative represented by the following formula (I):

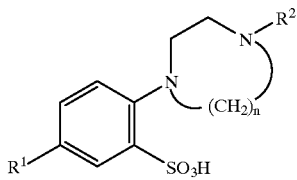

wherein $R^1$ represents a hydrogen atom, a $C_1$–$C_6$ alkyl group, a $C_3$–$C_7$ cycloalkyl group, a halogenated $C_1$–$C_4$ alkyl group, a halogen atom, or a $C_6$–$C_{12}$ aryl group; $R^2$ represents a hydrogen atom, a $C_1$–$C_6$ alkyl group, or a $C_7$–$C_{12}$ aralkyl group which may have one or more substituents selected from the group consisting of cyano group, nitro group, a $C_1$–$C_6$ alkoxy group, a halogen atom, a $C_1$–$C_6$ alkyl group, and amino group; and n represents an integer of from 1 to 4 (in the specification, the term "monohydrate" means a monohydrated crystal). According to a preferred embodiment of the invention, the monohydrate is of said aminobenzenesulfonic acid derivative wherein $R^1$ is a hydrogen atom or a $C_1$–$C_6$ alkyl group, $R^2$ is a hydrogen atom, and n is 2. A monohydrate of 2-(1-piperazinyl)-5-methylbenzenesulfonic acid is provided as a particularly preferred embodiment of the present invention.

According to another aspect of the present invention, there is provided a method for preparing the monohydrate of the aminobenzenesulfonic acid derivative represented by the above formula (I) which comprises the step in which an anhydrous crystal of said aminobenzenesulfonic acid derivative is suspended in water or an organic solvent containing water, or said anhydrous crystal is dissolved in water or an organic solvent containing water and the resulting solution is subjected to crystallization treatment, and then the crystal obtained is dried (in the specification, the term "anhydrous crystal" means an crystal having substantially no water of crystal). According to preferred embodiments of the above method, there are provided the method for preparing the monohydrate of the aminobenzenesulfonic acid derivative wherein $R^1$ is a hydrogen atom or a $C_1$–$C_6$ alkyl group, $R^2$ is a hydrogen atom, and n is 2; and the method for preparing the monohydrate of the aminobenzenesulfonic acid derivative wherein $R^1$ is methyl group, $R^2$ is a hydrogen atom, and n is 2.

According to further aspect of the present invention, there are provided a monohydrate of 2-(1-piperazinyl)-5-methylbenzenesulfonic acid obtainable by the step in which an anhydrous crystal of 2-(1-piperazinyl)-5-methylbenzenesulfonic acid is suspended in water or an organic solvent containing water, or said anhydrous crystal is dissolved in water or an organic solvent containing water and the resulting solution is subjected to crystallization treatment, and then the crystal obtained is dried; a pharmaceutical composition comprising the monohydrate of the aminobenzenesulfonic acid derivative represented by the above formula (I) as an active ingredient; and the above-defined pharmaceutical composition wherein said active ingredient is 2-(1-piperazinyl)-5-methylbenzenesulfonic acid.

DETAILED DESCRIPTION OF THE INVENTION

Figure 1:
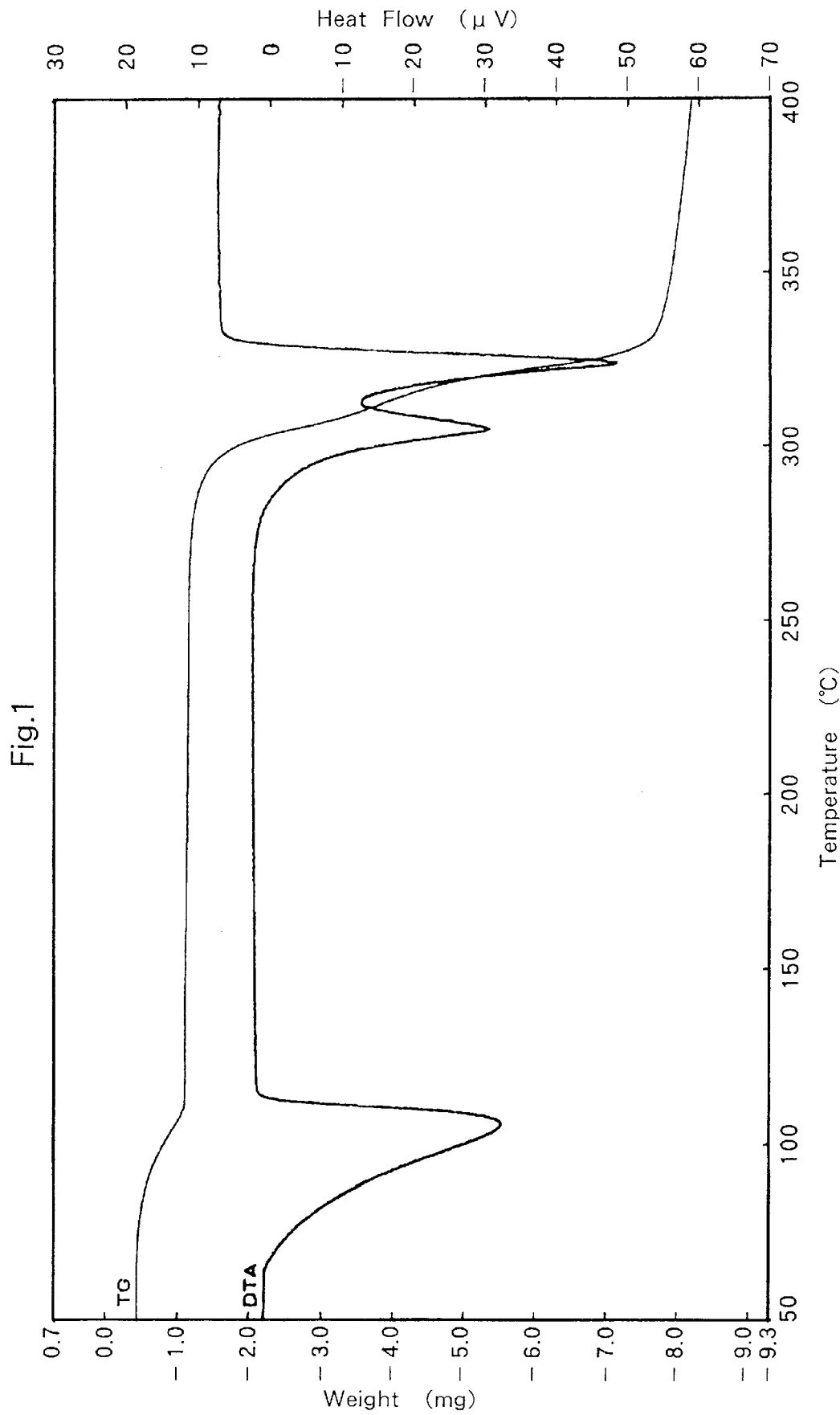
FIG. 1 shows the result of thermal analysis of the monohydrate of the present invention. In the figure, TG indicates the result of thermogravimetric analysis and DTA indicates the result of differential calorimetric analysis.

The monohydrates of the aminobenzenesulfonic acid derivatives are monohydrates of the compounds represented by the aforementioned formula (I). In the formula, examples of the $C_1$–$C_6$ alkyl group defined by $R^1$ include, for example, methyl group, ethyl group, propyl group, isopropyl group, butyl group, isobutyl group, sec-butyl group, tert-butyl group, pentyl group, isopentyl group, neopentyl group, tert-pentyl group, hexyl group, and isohexyl group. Examples of the $C_3$–$C_7$ cycloalkyl group include, for example, cyclopropyl group, cyclobutyl group, cyclopentyl group, cyclohexyl group, and cycloheptyl group. Examples of the halogenated $C_1$–$C_4$ alkyl group include, for example, trifluoromethyl group, trifluoroethyl group, and pentafluoroethyl group. Examples of the halogen atom include fluorine atom, chlorine atom, and bromine atom. Examples of the $C_6$–$C_{12}$ aryl group include, for example, phenyl group and naphthyl group.

Examples of the $C_1$–$C_6$ alkyl group defined by $R^2$ include, for example, methyl group, ethyl group, propyl group, isopropyl group, butyl group, isobutyl group, sec-butyl group, tert-butyl group, pentyl group, isopentyl group, neopentyl group, tert-pentyl group, hexyl group, and isohexyl group. Examples of the $C_7$–$C_{12}$ aralkyl group include, for example, benzyl group, phenethyl group, and naphthylmethyl group. The aralkyl group may have one or more substituents selected from the group consisting of cyano group; nitro group; a $C_1$–$C_6$ alkoxy group such as, for example, methoxy group, ethoxy group, propoxy group, isopropoxy group, butoxy group, isobutoxy group, tert-butoxy group, pentyloxy group, isopentyloxy group, tert-pentyloxy group, or hexyloxy group; a halogen atom such as fluorine atom, chlorine atom, or bromine atom; a $C_1$–$C_6$ alkyl group such as, for example, methyl group, ethyl group, propyl group, isopropyl group, butyl group, isobutyl group, sec-butyl group, tert-butyl group, pentyl group, isopentyl group, neopentyl group, tert-pentyl group, hexyl group and isohexyl group; and amino group.

A Preferred example of the monohydrates of the present invention includes the monohydrates of the compounds wherein $R^1$ is a hydrogen atom or a $C_1$–$C_6$ alkyl group, $R^2$ is a hydrogen atom, and n is 2 in the aforementioned formula (I). Preferred and specific examples of the monohydrates of the present invention include the monohydrates of the compounds listed in the Table 1 set out below.

TABLE 1

| Compound No. | $R^1$ | $R^2$ | n |
|---|---|---|---|
| 1 | H | H | 2 |
| 2 | $CH_3$ | H | 2 |
| 3 | $CH_2CH_3$ | H | 2 |
| 4 | $(CH_2)_2CH_3$ | H | 2 |
| 5 | $CH(CH_3)_2$ | H | 2 |
| 6 | $(CH_2)_3CH_3$ | H | 2 |
| 7 | $(CH_2)_4CH_3$ | H | 2 |
| 8 | $(CH_2)_5CH_3$ | H | 2 |
| 9 | Phenyl | H | 2 |
| 10 | H | H | 3 |
| 11 | $CH_3$ | H | 3 |
| 12 | $CH_2CH_3$ | H | 3 |
| 13 | $(CH_2)_2CH_3$ | H | 3 |
| 14 | $CH(CH_3)_2$ | H | 3 |
| 15 | $(CH_2)_3CH_3$ | H | 3 |
| 16 | $(CH_2)_4CH_3$ | H | 3 |
| 17 | $(CH_2)_5CH_3$ | H | 3 |
| 18 | Phenyl | H | 3 |
| 19 | H | $CH_3$ | 2 |
| 20 | $CH_3$ | $CH_3$ | 2 |
| 21 | $CH_2CH_3$ | $CH_3$ | 2 |
| 22 | $(CH_2)_2CH_3$ | $CH_3$ | 2 |
| 23 | $CH(CH_3)_2$ | $CH_3$ | 2 |
| 24 | Phenyl | $CH_3$ | 2 |
| 25 | H | $(CH_2)_2CH_3$ | 2 |
| 26 | $CH_3$ | $(CH_2)_2CH_3$ | 2 |
| 27 | $CH_2CH_3$ | $(CH_2)_2CH_3$ | 2 |
| 28 | $(CH_2)_2CH_3$ | $(CH_2)_2CH_3$ | 2 |
| 29 | $CH(CH_3)_2$ | $(CH_2)_2CH_3$ | 2 |
| 30 | Phenyl | $(CH_2)_2CH_3$ | 2 |
| 31 | H | Benzyl | 2 |
| 32 | $CH_3$ | Benzyl | 2 |
| 33 | $CH_2CH_3$ | Benzyl | 2 |
| 34 | $(CH_2)_2CH_3$ | Benzyl | 2 |
| 35 | $CH(CH_3)_2$ | Benzyl | 2 |
| 36 | $CH_3$ | 2-Cyanobenzyl | 2 |
| 37 | $(CH_2)_2CH_3$ | 2-Cyanobenzyl | 2 |
| 38 | $CH_3$ | 3-Nitrobenzyl | 2 |
| 39 | $(CH_2)_2CH_3$ | 3-Nitrobenzyl | 2 |
| 40 | $CH_3$ | 4-Methoxybenzyl | 3 |
| 41 | $(CH_2)_2CH_3$ | 4-Methoxybenzyl | 3 |
| 42 | $CH_3$ | 3,4-Dimethoxybenzyl | 3 |
| 43 | $(CH_2)_2CH_3$ | 3,4-Dimethoxybenzyl | 3 |
| 44 | $CH_3$ | 2-Fluorobenzyl | 3 |
| 45 | $(CH_2)_2CH_3$ | 3-Chlorobenzyl | 3 |
| 46 | $CH_3$ | 4-Bromobenzyl | 3 |
| 47 | $(CH_2)_2CH_3$ | 2-Methylbenzyl | 3 |
| 48 | $CH_3$ | 3-Ethylbenzyl | 3 |
| 49 | $(CH_2)_2CH_3$ | 4-Propylbenzyl | 2 |
| 50 | $CH_3$ | 3-Aminobenzyl | 2 |
| 51 | $(CH_2)_2CH_3$ | 4-Aminobenzyl | 2 |

The monohydrates of pharmaceutically acceptable salts of the aforementioned compounds also fall within the scope of the present invention. Examples of such salts include, for example, alkali metal salts and alkaline earth metal salts such as, for example, sodium salts, potassium salts, magnesium salts, calcium salts, or aluminum salts; ammonium salts; amine salts such as, for example, lower alkylamine salts such as triethylamine, hydroxy-lower alkylamine salts such as 2-hydroxyethylamine salts, bis-(2-hydroxyethyl) amine salts, tris(hydroxymethyl)aminomethane salts, or N-methyl-D-glucamine salts, cycloalkylamine salts such as dicyclohexylamine salts, benzylamine salts such as N,N-dibenzylethylenediamine salts, or dibenzylamine salts; inorganic acid salts such as, for example, hydrochloric acid salts, hydrobromic acid salts, sulfuric acid salts, or phosphoric acid salts; and organic acid salts such as, for example, fumaric acid salts, succinic acid salts, oxalic acid salts, or lactic acid salts.

An example of the more preferred embodiment of the present invention include, for example, the monohydrate of the compound of the formula (I) wherein $R^1$ is methyl group, $R^2$ is a hydrogen atom, and n is 2. The crystal of the monohydrate of 2-(1-piperazinyl)-5-methylbenzenesulfonic acid, provided as a particularly preferred embodiment of the present invention, is distinguishable from the anhydrous crystal of 2-(1-piperazinyl )-5-methylbenzenesulfonic acid disclosed as Compound No. 12 in Example 1 of the Japanese Patent Unexamined Publication (KOKAI) No. (Hei)3-7263/1991. The aforementioned monohydrate of the present invention is stable for a long period of time and the water of crystal will not be generally released when dried at room temperature. However, when heated under ambient pressure or reduced pressure at a temperature of 60° C. or higher, e.g., a temperature of from 100 to 120° C., the hydrate will gradually release the water of crystal to give the anhydrous crystal disclosed in Example 1 of the Japanese Patent Unexamined Publication (KOKAI) No. (Hei)3-7263/1991.

As for the monohydrate of 2-(1-piperazinyl)-5-methylbenzenesulfonic acid, a particularly preferred embodiment of the present invention, various physicochemical properties will be described in the section of Examples by referring to experimental values and spectrums. However, it should be understood that these experimental values and spectrums are described by way of a reference purpose. Whether or not a certain crystal falls within the monohydrate of the present invention should not be decided based on criteria whether or not the crystal gives completely the same experimental values and spectrums as those disclosed in the present specification. It will be readily understood by those skilled in the art that such experimental values and spectrums involve experimental errors due to factors including a measuring apparatus, a measuring process, and measuring conditions, and accordingly, the decision should be made based on a consideration of such experimental errors and using criteria whether or not the crystal has substantially the physicochemical properties set out below. Although the method for manufacturing the monohydrate of the present invention is not particularly limited, it may generally be manufactured by preparing anhydrous crystals of the compound of formula (I) according to the method disclosed in Example 1 of the Japanese Patent Unexamined Publication (KOKAI) No. (Hei)3-7263/1991, and then contacting the anhydrous crystals with water, moisture in a solvent, or moisture in air for a suitable period of time. However, for the preparation of the monohydrate of the present invention, it is preferable to use the method of the present invention as explained below.

According to another aspect of the present invention, there is provided a method for preparing the monohydrate of the aminobenzenesulfonic acid derivatives of formula (I), which comprises the step in which an anhydrous crystal of said aminobenzenesulfonic acid derivative is suspended in water or an organic solvent containing water, or said anhydrous crystal is dissolved in water or an organic solvent containing water and the resulting solution is subjected to crystallization treatment, and then the crystal obtained is dried. The aminobenzenesulfonic acid derivatives of formula (I), used as the starting materials of the present invention, can be prepared by the known method (the Japanese Patent Publication (KOKOKU) No. (Hei)6-86438/1994). For example, 5-methyl-2-(1-piperazinyl) benzenesulfonic acid can be obtained by reacting 2-fluoro-5-methyl benzenesulfonic acid and piperazine in a sealed tube under heating in the presence of cuprous iodide and copper powder. This compound corresponds to the compound of the formula (I) wherein $R^1$ is methyl group, $R^2$ is a hydrogen atom, and n is 2 (Compound No. 2 in Table 1).

The monohydrate of the aminobenzenesulfonic acid derivative can be obtained by suspending the aminobenzenesulfonic acid derivative represented by the formula (I) in water or a water-containing organic solvent, and recovering the resulting crystals by filtration and drying the crystals. As the organic solvent, water-miscible solvents such as methanol, ethanol, 2-propanol, acetone, and tetrahydrofuran can be used. The suspending treatment may preferably be carried out with stirring and a temperature for the treatment may be in a range of from an ambient temperature to a temperature under heating, preferably at 35° C. or less, and an ambient temperature may be sufficient. The volume of water or the water-containing organic solvent is not particularly limited, and may be chosen so as to sufficiently immerse the aminobenzenesulfonic acid derivative of the above formula (I). Generally, the solvent may used in an amount of 1 to 50 times (V/W) of the weight of the aminobenzenesulfonic acid derivative of the formula (I). Although a water content ratio in the water-containing organic solvent is not particularly limited, water should be used in an equimolar amount or more of the aminobenzenesulfonic acid derivative of the above formula (I). The time for the suspension treatment may generally be 1 hour or more, preferably 2 hours or more, although a shorter time may be sufficient. After the completion of the suspending treatment, the resulting crystals are collected by filtration and then dried to give the monohydrate of the present invention. The pressure and the temperature for the drying process may appropriately determined in consideration of a bond strength of the water of crystal, constituting the monohydrate, to the crystal (i.e., a stability of the monohydrate). The completion of the drying process may be determined by observing a ceasation of weight alteration (i.e., a decrease) of the crystals.

The monohydrate of the aminobenzenesulfonic acid derivative of the present invention can also be prepared by subjecting a solution, obtained by dissolving the aminobenzenesulfonic acid derivative of the above formula (I) in water or a water-containing organic solvent, to a crystallizing treatment and then recovering the resulting crystals by filtration and drying the crystals. Examples of the crystallizing treatment include, for example, (a) a process comprising the step of dissolving the aminobenzenesulfonic acid derivative of the above general formula (I) in water or a water-containing organic solvent under heating or under reflux with stirring, and then cooling the solution to allow the precipitation and growing of the crystals; (b) a process comprising the step of dissolving the aminobenzenesulfonic acid derivative of the above general formula (I) in a basic or a acidic aqueous solution or water-containing organic solvent, and then adjusting the hydrogen ion concentration using an acid or a base to allow the precipitation and growing of the crystals; or (c) dissolving the aminobenzenesulfonic acid derivative of the above general formula (I) in water or a water-containing organic solvent, and then adding a solvent which reduces the solubility of the aminobenzenesulfonic acid derivative of the above general formula (I) to allow the precipitation and growing of the crystals.

As the organic solvent, water-miscible organic solvents such as methanol, ethanol, 2-propanol, acetone, or tetrahydrofuran can be used. As the acid, mineral acids such as hydrochloric acid or sulfuric acid, or organic acids such as acetic acid, methanesulfonic acid, or p-toluenesulfonic acid may be used, and as the base, alkali metal or alkaline earth metal salts such as lithium hydroxide, sodium hydroxide, potassium hydroxide, barium hydroxide, calcium hydroxide, sodium carbonate, potassium carbonate, sodium hydrogen carbonate, or potassium hydrogen carbonate, or organic bases such as pyridine or triethylamine may be used. These acids and bases may be used as solutions diluted or dissolved with water or organic solvents. The temperature applied to dissolve the aminobenzenesulfonic acid derivative of the above general formula (I); the amount the water, the water-containing organic solvent, the basic solvent, or the acidic solvent; the amount of an acid or a base used to adjust the hydrogen ion concentration; and a temperature for the growing of the precipitated crystals may suitably be chosen in consideration of the solubility of the aminobenzenesulfonic acid derivative of the above general formula (I) in the solvent used.

In the above process (a), the temperature applied to dissolve the aminobenzenesulfonic acid derivative of the above general formula (I) may preferably be, for example, the refluxing temperature of the solvent, and the volume of water or water-containing organic solvent may preferably be the minimum volume required to completely dissolve the aminobenzenesulfonic acid derivative of the above general formula (I) at the refluxing temperature of the solvent. The temperature applied to the growing of the crystals may preferably be an ambient temperature or less, more preferably 25° C. or less. The water content ratio of the water-containing organic solvent is not particularly limited, and may be suitably chosen in consideration of the solubility of the aminobenzene-sulfonic acid derivative of the above general formula (I) in the solvent. The period of time for the growing of the precipitated crystals may generally be 1 hour or more, preferably 2 hours or more. After the completion of the growing, the crystals are collected by filtration and dried to obtain the monohydrate of the present invention. The drying process may be carried out according to the methods explained above.

Where the monohydrates of the present invention are the monohydrates of the salts of the compounds of the above formula (I), the monohydrates of the present invention may be prepared by processes such as, for example, a process comprising the step of preparing the salt of the aminobenzenesulfonic acid derivative of the above formula (I) by an ordinary method, and then preparing the monohydrate of the resulting salt according to the method described above; a process comprising the step of preparing the monohydrate of the compound in the free form according to the method of the present invention, and then converting the product to the monohydrate of the salt by an ordinary method: or a process comprising the step of preparing the salt by an ordinary method simultaneously in the process of preparing the monohydrate according to the method of the present invention.

The monohydrates of the present invention are characterized in that they are substantially free from water absorption and/or hygroscopicity. Accordingly, for example, by using the monohydrate of 2-(1-piperazinyl)-5-methylbenzenesulfonic acid of the present invention as an active ingredient of a pharmaceutical composition, instead of the anhydrous crystal of 2-(1-piperazinyl)-5-methylbenzenesulfonic acid disclosed in Example 1 of the Japanese Patent Unexamined Publication (KOKAI) No. (Hei)3-7263/1991, it becomes possible to accurately weigh the active ingredient, and a pharmaceutical composition having a constant content of the active ingredient can be provided.

The monohydrates of the present invention are useful for the manufacture of pharmaceutical compositions used for the preventive and therapeutic treatment of ischemic heart diseases such as myocardial infarction or angina pectoris, cardiac failure, hypertension, arrhythmia and the like. The forms of the pharmaceutical compositions are not particularly limited, and examples include, for example, formulations for oral administration such as, for example, tablets, capsules, powders, subtilized granules, granules, solutions, or syrups, or formulations for parenteral administration such as, for example, injections, drip infusions, suppositories, inhalants, patches.

For the manufacture of the above pharmaceutical compositions, pharmacologically and pharmaceutically acceptable additives may optionally be used. For the preparation of the pharmaceutical compositions suitable for oral, transdermal, or transmucosal administration, for example, excipients such as glucose, lactose, D-mannitol, starch, or crystalline cellulose; disintegrator or disintegrating aids such as carboxymethylcellulose, starch, or carboxymethylcellulose calcium; binders such as hydroxypropylcellulose, hydroxypropylmethylcellulose, polyvinylpyrrolidone, or gelatin; lubricants such as magnesium stearate or talc; coating agents such as hydroxypropylmethylcellulose, saccharose, polyethylene glycol, or titanium oxide; bases such as vaseline, liquid paraffin, polyethylene glycol, gelatin, china clay, glycerin, purified water, or hard fat. Pharmaceutical additives such as, for example, propellants such as flons, diethyl ether, or compressed gases; adhesives such as sodium polyacrylate, polyvinyl alcohol, methylcellulose, polyisobutylene, or polybutene; or base cloths such as cotton cloths or plastic sheets may also be used.

For the manufacture of the pharmaceutical compositions suitable as injections or drip infusions, pharmaceutical additives such as, for example, dissolving agents or dissolving aids which can form aqueous injections or injections dissolved before use such as distilled water for injection, physiological saline, or propylene glycol; isotonic agents such as glucose, sodium chloride, D-mannitol, or glycerin; pH modifiers such as inorganic acids, organic acid, inorganic bases, or organic bases may be used.

The present invention will be more specifically explained by referring to the following examples. However, the scope of the present invention is not limited to the following examples.

EXAMPLES

Example 1
Preparation of the Monohydrate of the Present Invention (a) According to the method described in Example 1 of the Japanese Patent Unexamined Publication (KOKAI) No. (Hei)3-7263/1991, 2-fluoro-5-methylbenzenesulfonic acid (0.76 g) and piperazine (3.44 g) were reacted in a sealed tube in the presence of cuprous iodide (0.76 g) and copper powder (0.26 g) at 160° C. for 8 hours, and then the reaction product was purified by silica gel chromatography (eluent: chloroform: methanol: acetic acid=100:100:3) to give anhydrous crystals of 2-(1-piperazinyl)-5-methylbenzenesulfonic acid (0.67 g, yield: 65.0%).

(b) The anhydrous crystals obtained in the above process (a) (0.4506 g) and distilled water (1.35 ml) were added in a 5 ml round-bottomed flask and the mixture was stirred at 5° C. for 2 hours. The crystals were recovered from the suspension by suction filtration, and then crystals remaining in the round-bottomed flask were recovered by washing with the filtrate. The crystals were combined and dried at 50° C. and 90 mmHg for 3 hours to obtain 5-methyl-2-(1-piperazinyl)benzenesulfonic acid monohydrate as white crystals (0.4485 g, yield: 93.0%). From the result of the elemental analysis set out below, the compound was verified as the monohydrate. Elemental analysis

| | |
|---|---|
| Calcd. for monohydrate | C:48.16, H:6.617 N:10.21, S:11.69 |
| Found | C:48.16, H:6.55, N:10.09, S:11.87 |
| Calcd. for anhydrous crystal (as a reference) | |
| | C:51.54, H:6.29, N:10.93, S:12.51 |

Example 2
Thermal Analysis of the Monohydrate of the Present Invention (TG-DTA)

The anhydrous crystal described in Example 1 of the Japanese Patent Unexamined Publication (KOKAI) No. (Hei)3-7263/1991 and the monohydrate of the present invention were subjected to thermal analysis by a thermal analyzer (RIGAKU TAS-200) under dry nitrogen atmosphere using each of 10 mg of samples. The measurements were carried out in the temperature range of from 50 to 400° C. applying the temperature raising rate of 5° C./min. As the anhydrous crystals, those obtained in the above process (a) was used.

Figure 2:
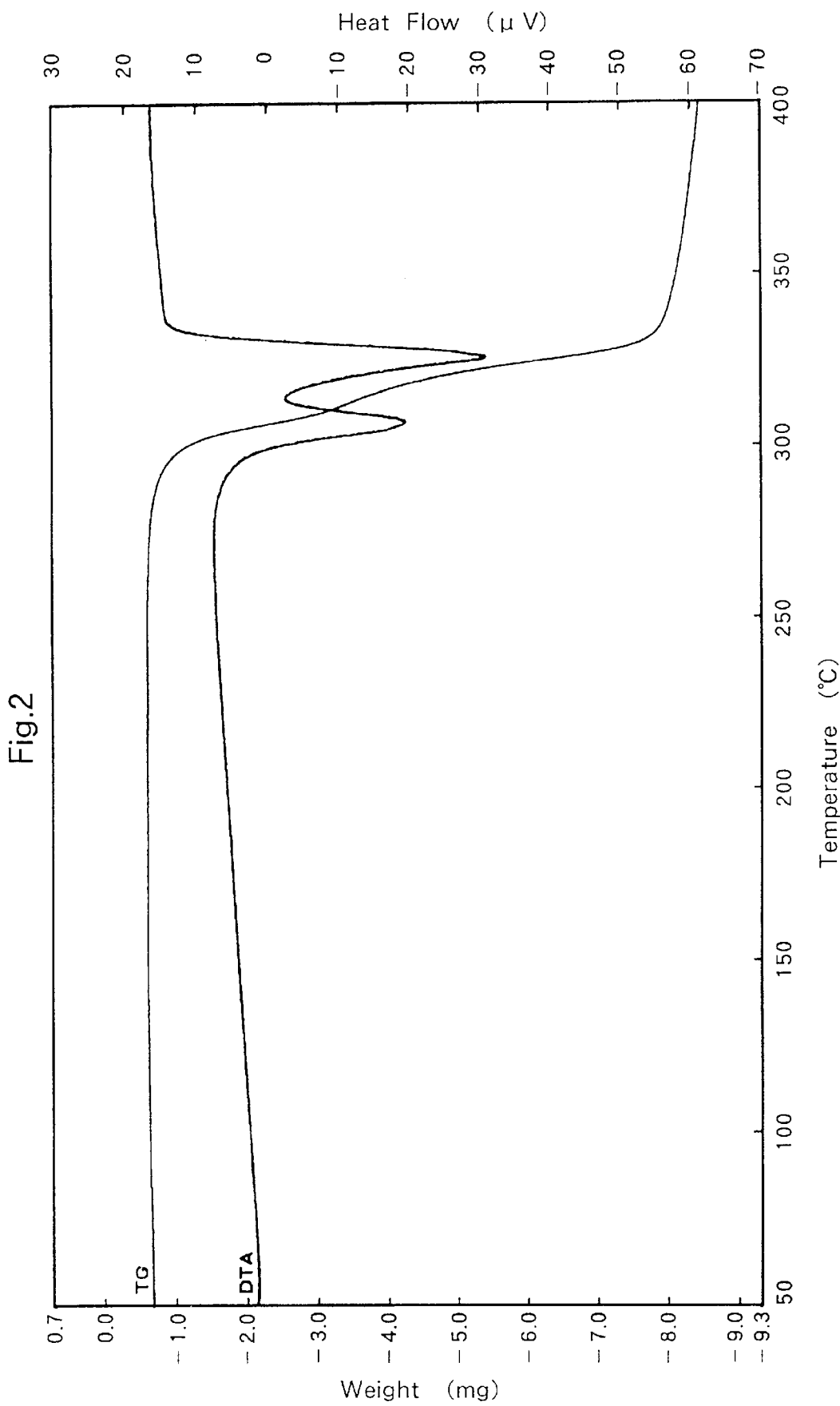
FIG. 2 shows the result of thermal analysis of the anhydrous crystal disclosed in Example 1 of the Japanese Patent Unexamined Publication (KOKAI) No. (Hei)3-7263/1991. In the figure, TG indicates the result of thermogravimetric analysis and DTA indicates the result of differential calorimetric analysis.

For the monohydrate of the present invention, a weight loss and a thermal absorption peak due to the release of the water of crystal were observed from around 60° C. The weight loss was 6.57%, which corresponded to the release of one molecule of water. Thermal absorption peaks accompanied by weight losses were also observed around 300° C. and 320° C. (FIG. 1). On the other hand, the anhydrous crystal exhibited thermal absorption peaks accompanied by weight losses around 300° C. and 320° C., but no weight loss or no thermal absorption peak due to the release of the water of crystal was observed at temperatures below 100° C. (FIG. 2). A sample was prepared, in situ, by heating the monohydrate obtained in the above process (b) in the thermal analyzer by heating up to 110° C. to remove the water of crystal, and after cooling to room temperature, the thermal analysis was carried out using the converted weight. The results were the same as those obtained by the anhydrous product (FIG. 2).

Figure 3:
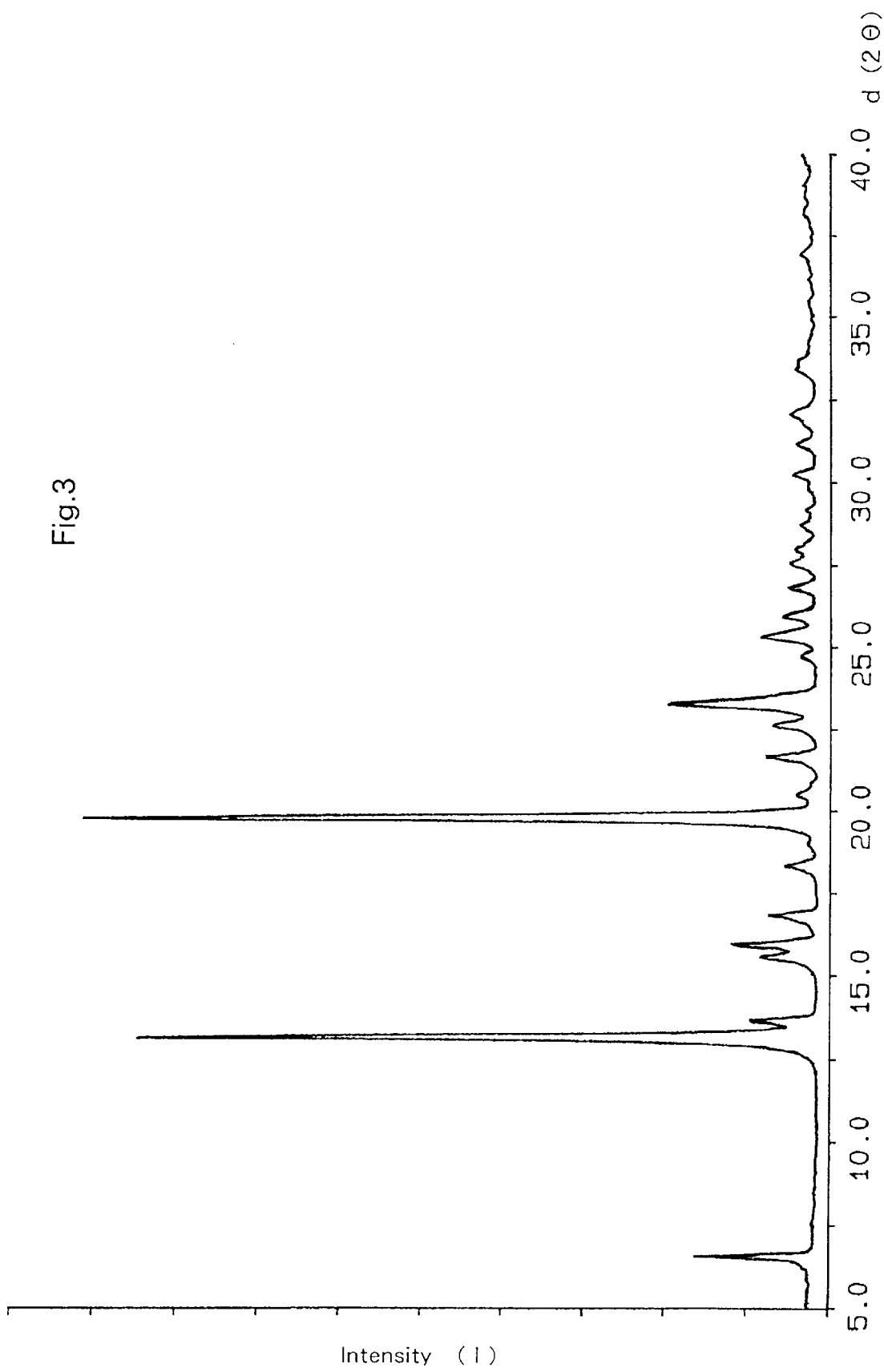
FIG. 3 shows powder X-ray diffraction pattern of the monohydrate of the present invention. In the figure, the abscissa axis indicates lattice spacing (d, angstrom) and the ordinate axis indicates intensity (I).
Figure 4:
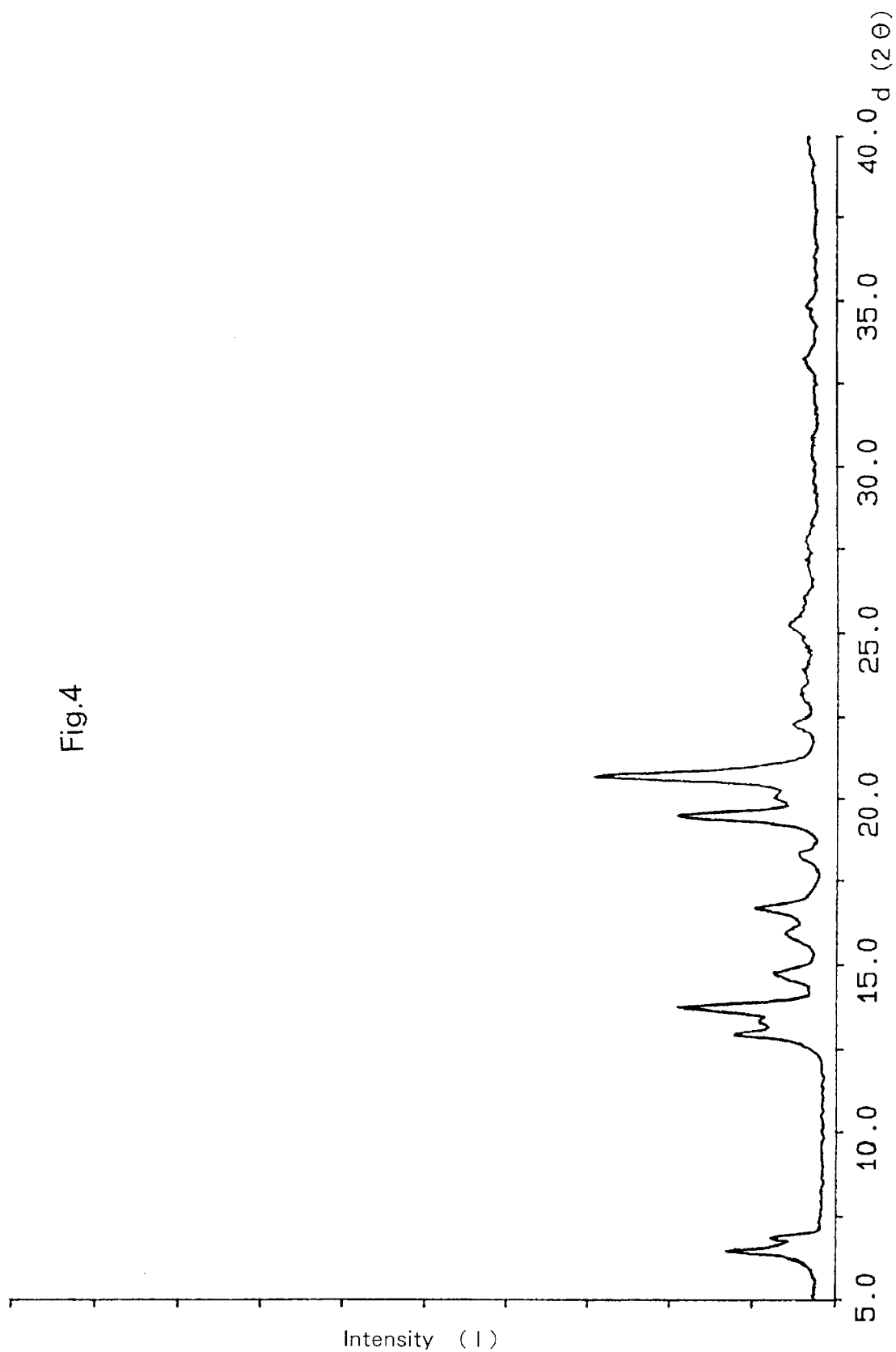
FIG. 4 shows powder X-ray diffraction pattern of the anhydrous crystal disclosed in Example 1 of the Japanese Patent Unexamined Publication (KOKAI) No. (Hei)3-7263/1991. In the figure, the abscissa axis indicates lattice spacing (d, angstrom) and the ordinate axis indicates intensity (I).

Example 3
X-ray Diffraction Analysis of the Monohydrate of the Present Invention Powder X-ray diffraction analysis of the monohydrate of the present invention was performed at room temperature under dried nitrogen gas flow (50 ml/min) using an X-ray diffractometer (Philips, PW 1700). The powder diffraction profile obtained is shown in FIG. 3. Powder X-ray diffraction analysis of the anhydrous crystal obtained in the above process (a) in Example 1 was also carried out under the same conditions. The resulting powder diffraction profile is shown in FIG. 4. The monohydrate and the anhydrous crystal gave distinguishable powder diffraction profiles, which verified that these crystalline powders were different from each other. After the analysis of the monohydrate, the sample was heated to 110° C. to prepare anhydrous crystals, in situ. After cooling to 25° C., powder X-ray diffraction analysis was carried out, and as a result, the same powder diffraction profile as that shown in FIG. 4 was obtained.

Example 4
Hygroscopic Property of the Monohydrate of the Present Invention

Each of the samples of the monohydrate of the present invention was put in a desiccator adjusted at a relative humidity of 57% or 98%, and then stored at 20° C. for 16 days. Weight changes during the period of time were measured. As controls, the anhydrous crystals obtained in the above process (a) in Example 1 were also stored in a desiccator adjusted at a relative humidity of 57% or 98%, and weight changes were measured. The results are shown in Table 2 [in the table, each of the values (%) represents a weight increase]. No substantial weight change was observed in the monohydrate under both of the relative humidity conditions. On the other hand, as for the anhydrous crystal, the weight increase of about 7% was observed, which corresponded to about 1 mole of the water of crystal.

TABLE 2

| Crystal | $RH^1$ (%) | 0 day | 1 day | 3 days | 16 days |
|---|---|---|---|---|---|
| Anhydrous crystal | 57 | 0.00 | 6.99 | 7.08 | 6.89 (%) |
| Anhydrous crystal | 98 | 0.00 | 7.35 | 7.36 | 7.12 |
| Monohydrate | 57 | 0.00 | 0.11 | 0.20 | 0.21 |
| Monohydrate | 98 | 0.00 | 0.28 | 0.40 | 0.39 |

[1]RH: relative humidity (%)

Example 5
Serum Concentration (1)

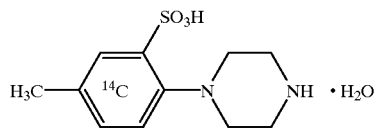

A labeled 2-(1-piperazinyl)-5-methylbenzenesulfonic acid monohydrate represented by the above formula (II) (hereinafter referred to as "labeled compound") was orally administered to male rats (n=3) at a dose of 1 mg/kg corresponding to 0.94 mg/kg of the anhydrous crystal of 2-(1-piperazinyl)-5-methylbenzenesulfonic acid (hereinafter referred to as "anhydrous crystal"). Radioactivities in the serum were measured and AUC(0–∞) was calculated (1039.86 ng eq·h/ml). The labeled compound was also administered intravenously to male rats (n=3) at a dose of 0.3 mg/kg (corresponding to 0.28 mg/kg of the anhydrous crystal) and radioactivities in the serum were measured to calculate AUC(0–∞) (816.28 ng eq·h/ml). Using these values of AUC(0–∞) and the doses applied, the bioavailability was calculated according to the following Equation 1.

$$\text{Bioavailability} = \frac{AUC(0 - \infty) \text{ for oral administration}}{AUC(0 - \infty) \text{ for intravenous administration}} \times \frac{\text{dose for intravenous}}{\text{dose for oral administration}} \times 100 \quad \text{(Equation 1)}$$

$$= \frac{1039.86}{816.28} \times \frac{0.28}{0.94} \times 100 = 38 \ (\%)$$

Example 6
Serum Concentration (2)

Figure 5:
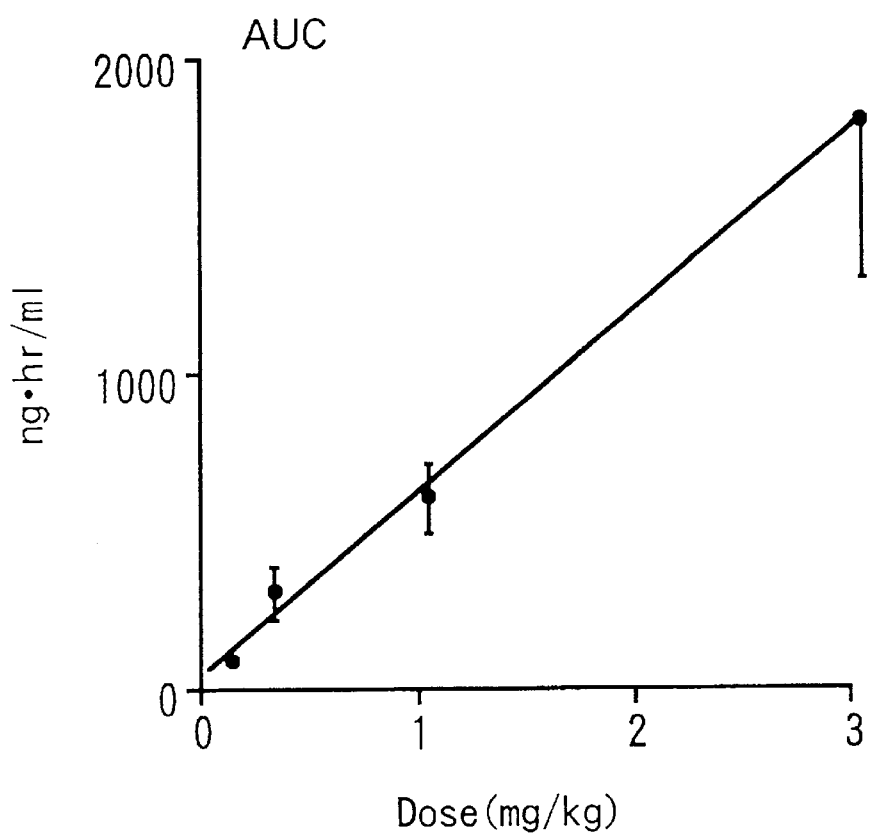
FIG. 5 shows the correlation between the dose and AUC for the course of serum radioactivity concentration when a single oral administration of the labeled monohydrate of the present invention was given to male rats.
Figure 6:
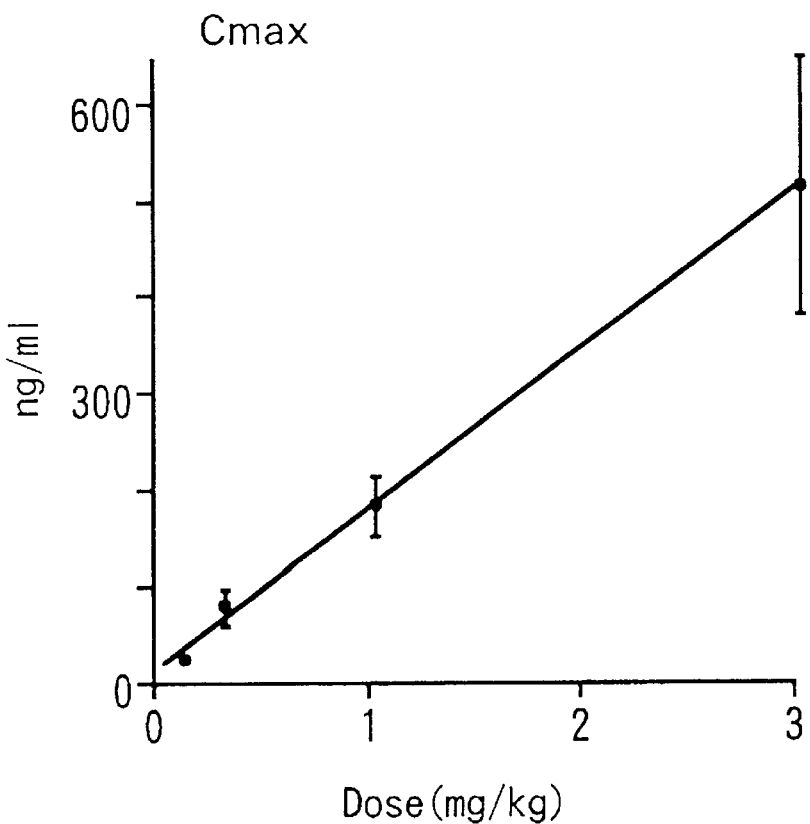
FIG. 6 shows the correlation between the dose and Cmax for the course of serum radioactivity concentration when a single oral administration of the labeled monohydrate of the present invention was given to male rats.

The labeled compound was orally administered to male rats (n=5) at a dose of 0.1 mg/kg, 0.3 mg/kg, 1 mg/kg, or 3 mg/kg (0.094 mg/kg, 0.28 mg/kg, 0.94 mg/kg or 2.8 mg/kg corresponding to the anhydrous crystals, respectively) and radioactivities in serum were observed. Tmax, Cmax, t1/2, and AUC calculated from the course of the serum radioactivities are summarized in Table 3. Correlations between the AUC and the dose, and between the Cmax and the dose are shown FIGS. 5 and 6.

TABLE 3

| Dose (mg/kg) | T max (hr) | C max (ng/ml) | t ½ (hr) | AUC (ng · hr/ml) |
|---|---|---|---|---|
| 0.1 | 2.2 ± 0.5 | 16.2 ± 2.6 | 1.77 ± 0.34 | 64.1 ± 12.3 |
| 0.3 | 2.2 ± 0.5 | 69.0 ± 17.8 | 1.33 ± 0.09 | 270.5 ± 88.4 |
| 1 | 1.8 ± 0.5 | 171.6 ± 31.1 | 1.64 ± 0.17 | 574.4 ± 113.2 |
| 3 | 2.0 ± 0.0 | 501.5 ± 133.8 | 1.30 ± 0.08 | 1769.2 ± 498.4 |

Mean ± S.D (n = 5)

As shown in Example 4, the anhydrous crystal exhibited about 7% of weight change (one molecule of water corresponds to about 7% of the total weight of the monohydrate of 2-(1-piperazinyl)-5-methylbenzenesulfonic acid). Apparently, the anhydrous crystal causes approximately the maximum 7% of weight change by hydration due to moisture absorption in course of time. Therefore, where crystals obtained as the anhydrous crystals are measured, administration doses of the active substance may be varied in a range of from 93 to 100% depending on the degree of the hydration, since the degree of hydration due to the moisture absorption is unknown. On the other hand, if the crystals are weighed as the monohydrate, administration doses of the active substance may be varied in a range of from 100 to 107% by the same reason. Accordingly, the weighing process of the anhydrous crystal may cause fluctuation of the dose of the active substance within a range of from 93 to 107% with respect to an intended dose.

As shown in Example 6, the serum concentration of the monohydrate of the present invention exhibits linear direct proportion to the dose of administration. Accordingly, if the anhydrous crystal is weighed and administered, the serum concentration may similarly fluctuate within the span of 14%. In consideration of the calculation of the oral absorbability in Example 5, the absorbability is provided by Equation 1, and therefore, the values as the denominator and the numerator of Equation 1 which represent the doses may fluctuate independently. When the average of the fluctuated bioavailability is considered as 38%, the following results are obtained:

Maximum value=(107%/93%)×38%=43.72%

Minimum value=(93%/107%)×38%=33.03%.

The results indicate that the range of fluctuation of the bioavailability may be expanded to 33.03~43.72% (difference=10.69%).

In contrast, the monohydrates of the present invention are stable and free from the fluctuations as mentioned above. Accordingly, the monohydrates of the present invention have advantages that determination of a dose for desired efficacy and the assurance of safe range of administration can easily be conducted, and various administration routes can be chosen. In addition, for example, when the monohydrate of the present invention is used as a medicament for clinical treatment of a patient in a condition of cardiac failure, it is clinically very important to accurately measure the effect of improvement of cardiac functions and appropriately control the dose depending on the improved conditions. By using the monohydrate of the present invention, the serum concentration of the drug can properly be maintained and the production of the effect can be controlled.

Example 7
Preparation of the Monohydrate in a Steam Moistened Room

Steam was generated by heating a bath filled with water at 50° C. in a plastic sheet housing isolated from outer air. The anhydrous crystal of 5-Methyl-2-(1-piperazinyl) benzenesulfonic acid (4886.16 g) prepared by the method described in the Japanese Patent Unexamined Publication (KOKAI) No.(Hei)3-7263/1991 was spread in a stainless flat container and left in the above plastic sheet housing. The crystals were occasionally dispersed and sweat formed on inner wall of the housing and the stainless container was wiped. After 22.5 hours, weight increase ceased and 5217.65 g in total of 5-methyl-2-(1-piperazinyl)benzenesulfonic acid monohydrate was obtained as white crystals. The result of the elemental analysis verified that the crystals were the monohydrate crystals.

Elemental Analysis

| | |
|---|---|
| Calcd. for anhydrous crystal | C:51.54, H:6.29, N:10.93, S:12.51 |
| Calcd. for monohydrate | C:48.16, H:6.61, N:10.21, S:11.69 |
| Found | C:47.98, H:6.77, N:10.22, S:11.53 |

Example 8
Preparation of the Monohydrate by the Process of Suspension in Water The anhydrous crystal of 5-Methyl-2-(1-piperazinyl) benzenesulfonic acid (10.00 g) and distilled water (30 ml) were added in a 100 ml round-bottomed flask and the mixture was stirred at 5° C. for 2 hours. The crystals were collected from the suspension by suction filtration and the crystals remained in the round-bottomed flask were recovered by washing with distilled water (3 ml). The crystals were combined and dried at 50° C. and 90 mmHg for 3 hours to give 5-methyl-2-(1-piperazinyl)benzenesulfonic acid monohydrate as white crystals (10.36 g, yield: 96.8%). After drying was further continued for 27 hours under the same conditions, the weight and appearance of the monohydrate were not changed. Water content measured by a Karl Fischer water content meter was 6.96%, which further verified that the product was the monohydrate (calculated content: 6.56%).

Example 9
Preparation of Monohydrate by the Process of Crystallization from Water The anhydrous crystal of 5-Methyl-2-(1-piperazinyl) benzenesulfonic acid (10.00 g) and distilled water (75 ml) were charged in a 200 ml round-bottomed flask and the crystals were thoroughly dissolved by heating under reflux with stirring. The solution was then cooled to 5° C. with stirring and stirring was further continued for 2 hours at the same temperature. The precipitated crystals were collected by suction filtration and washed with distilled water (2 ml). The crystals obtained were dried at 50° C. under 90 mmHg for 3 hours to give 5-methyl-2-(1-piperazinyl)benzenesulfonic acid monohydrate as white crystals (9.46 g, yield: 87.8%). After drying was further continued for 27 hours under the same conditions, the weight and the appearance of the monohydrate were not changed. Water content measured by a Karl Fischer water content meter was 6.75%, which further verified that the product was the monohydrate.

Example 1
Preparation of Monohydrate by the Process of Crystallization from Water-containing Ethanol The anhydrous crystal of 5-Methyl-2-(1-piperazinyl) benzenesulfonic acid (10.00 g) and ethanol containing 50% (V/V) water (80 ml) were added in a 200 ml round-bottomed flask and the crystals were thoroughly dissolved by heating under reflux with stirring. The solution was then cooled to 5° C. with stirring and stirring was further continued for 2 hours at the same temperature. The precipitated crystals were collected by suction filtration and washed with ethanol containing 50% (V/V) water (20 ml). The crystals obtained were dried at 50° C. under 90 mmHg for 3 hours to give 5-methyl-2-(1-piperazinyl)benzenesulfonic acid monohydrate as white crystals (9.49 g, yield: 88.7%). After drying was further continued for 27 hours under the same conditions, the weight and the appearance of the monohydrate were not changed. Water content measured by a Karl Fischer water content meter was 6.74%, which further verified that the product was the monohydrate.

The monohydrate of the aminobenzenesulfonic acid derivatives, preferably, the monohydrate of 2-(1-piperazinyl)-5-methylbenzenesulfonic acid, provided by the present invention are stable at room temperature for a long period of time. The monohydrates of the present invention have substantially no weight change due to moisture absorption, and can be weighed accurately. Accordingly, pharmaceutical compositions having constant contents of the aminobenzenesulfonic acid derivatives as active ingredients, preferably 2-(1-piperazinyl)-5-methylbenzenesulfonic acid, can be prepared. In addition, according to the methods of the present invention, the monohydrate of the aminobenzenesulfonic acid derivatives useful for the treatment of heart diseases can be conveniently and reproducibly manufactured.

What is claimed is:

1. A monohydrate of 2-(1-piperazinyl)-5-methylbenzenesulfonic acid substantially free of anhydrous crystals.

2. A method for preparing the monohydrate of 2-(1-piperazinyl)-5-methylbenzenesulfonic acid substantially free of anhydrous crystals which comprises suspending an anhydrous crystal of said aminobenzenesulfonic acid derivative in water or an organic solvent containing water, or dissolving said anhydrous crystal in water or an organic solvent containing water and subjecting the resulting solution to crystallization treatment, and drying the monohydrate crystal thus obtained.

3. A monohydrate of 2-(1-piperazinyl)-5-methylbenzenesulfonic acid substantially free of anhydrous crystals prepared according to the process as defined in claim 2.

4. A pharmaceutical composition comprising as an active ingredient a pharmaceutically effective amount of a monohydrate of 2-(1-piperazinyl)-5-methylbenzene-sulfonic acid substantially free of anhydrous crystals and a pharmaceutically acceptable carrier therefor.

5. A method for the manufacture of a pharmaceutical composition as defined in claim 4 which comprises admixing a monohydrate of 2-(1-piperazinyl)-5-methylbenzenesulfonic acid substantially free of anhydrous crystals with a pharmaceutically acceptable carrier therefor.

* * * * *